(12) United States Patent
Peng et al.

(10) Patent No.: US 11,690,681 B2
(45) Date of Patent: Jul. 4, 2023

(54) METHOD FOR BONE REGISTRATION AND SURGICAL ROBOT

(71) Applicant: Suzhou MicroPort Orthobot Co., Ltd., Jiangsu (CN)

(72) Inventors: Weili Peng, Jiangsu (CN); Zhou Jiang, Jiangsu (CN); Feng Sun, Jiangsu (CN); Chao He, Jiangsu (CN); Tao Li, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 498 days.

(21) Appl. No.: 16/842,208

(22) Filed: Apr. 7, 2020

(65) Prior Publication Data
US 2021/0196397 A1 Jul. 1, 2021

(30) Foreign Application Priority Data
Dec. 26, 2019 (CN) .......................... 201911368137.1

(51) Int. Cl.
*A61B 34/20* (2016.01)
*A61B 34/10* (2016.01)
*A61B 34/37* (2016.01)
*G06T 7/33* (2017.01)

(52) U.S. Cl.
CPC .............. *A61B 34/20* (2016.02); *A61B 34/10* (2016.02); *A61B 34/37* (2016.02); *G06T 7/344* (2017.01); *A61B 2034/105* (2016.02); *A61B 2034/107* (2016.02); *A61B 2034/207* (2016.02); *A61B 2034/2055* (2016.02);
(Continued)

(58) Field of Classification Search
None
See application file for complete search history.

(56) References Cited

U.S. PATENT DOCUMENTS

| 2017/0277285 A1 | 9/2017 | Chung et al. |
| 2018/0177383 A1* | 6/2018 | Noonan ................. A61B 34/74 |
| 2018/0263714 A1* | 9/2018 | Kostrzewski ...... A61B 17/1703 |

(Continued)

FOREIGN PATENT DOCUMENTS

| CN | 104626168 A | 5/2015 |
| CN | 109443207 A | 3/2019 |

(Continued)

*Primary Examiner* — Tamara L Weber
(74) *Attorney, Agent, or Firm* — Muncy, Geissler, Olds & Lowe, P.C.

(57) ABSTRACT

The present disclosure provides a surgical robot including a control system, a force identification system, a robotic arm system and a navigation system, the robotic arm system including a robotic arm, a robotic arm terminal detachably connected to a trackable element. The navigation system acquires and provides a registration point of interest on an object to the robotic arm system. The robotic arm system controls movements of the robotic arm to drive the trackable element to move to the registration point of interest. The force identification system detects and provides a force applied to the robotic arm terminal to the control system. The control system determines whether the trackable element has moved to the registration point of interest on the object. The present disclosure also provides a method for bone registration of the surgical robot.

18 Claims, 11 Drawing Sheets

(52) U.S. Cl.
CPC ............... *A61B 2034/2059* (2016.02); *G06T 2207/20084* (2013.01); *G06T 2207/30008* (2013.01)

(56) References Cited

U.S. PATENT DOCUMENTS

| | | | |
|---|---|---|---|
| 2019/0125457 A1* | 5/2019 | Parihar | A61B 90/98 |
| 2020/0229878 A1* | 7/2020 | Finley | A61B 34/30 |
| 2021/0315591 A1* | 10/2021 | Herregodts | A61B 17/14 |

FOREIGN PATENT DOCUMENTS

| | | |
|---|---|---|
| CN | 109500837 A | 3/2019 |
| CN | 110103217 A | 8/2019 |
| CN | 110394801 A | 11/2019 |
| CN | 110547873 A | 12/2019 |
| CN | 111035454 A | 4/2020 |

\* cited by examiner

METHOD FOR BONE REGISTRATION AND SURGICAL ROBOT

CROSS-REFERENCE TO RELATED APPLICATION

This application claims the priority of Chinese patent application number 201911368137.1, filed on Dec. 26, 2019, the entire contents of which are incorporated herein by reference.

TECHNICAL FIELD

The present disclosure relates to the technical field of medical devices, and in particular, to a method for bone registration and a surgical robot.

BACKGROUND

Computer-assisted navigation system has become an important part of modern surgical technology, which helps operators perform various complex operations more accurately and safely. It has many irreplaceable advantages in all aspects of orthopedics, and has been widely used in clinical practice due to the accuracy, safety, low radiation or the like. It can also be used to direct operators in surgical training, formulate surgical plans, navigate surgical instruments in real time, and reduce patient trauma. In the field of artificial joint replacement, computer assistance results in a more accurate osteotomy and prosthesis installation, and a post-operative force line recovery more close to the physiological state.

Generally, a surgical robot is required to perform a bone registration to establish a corresponding relationship between a physical bone and a virtual image, which provides three-dimensional information to an operator for the osteotomy, bone surface treatment, and prosthesis placement. Taking operation of knee osteotomy as an example, in a conventional method, the operator holds the trackable element by hand and selects a registration point on the patient's bone to complete the bone registration. However, in the case that the trackable element is operated by the operator, it is difficult for the operator to accurately control the insertion depth into cartilage. As a result, the registration point on the bone cannot be correctly selected, which reduces the accuracy of bone registration. Moreover, the manual registration process is time-consuming, inefficient, and easy to cause registration deviation.

Therefore, it is necessary to provide a surgical robot and registration method that can automatically complete or assist in completing the bone registration process and improve the accuracy and efficiency of bone registration.

SUMMARY

To achieve the above object, the present disclosure provides a method for bone registration of a surgical robot and a surgical robot, which are able to automatically complete or assist the operator in completing the bone registration process, improve the efficiency of bone registration, help the operator in reducing workload, and in particular, to identify the force applied to the robotic arm terminal to ensure accurate selection of the registration point on the bone, improving the accuracy and safety of bone registration.

According to an aspect of the present disclosure, there is provided a method for bone registration of a surgical robot, including:

selecting a registration point of interest on an object according to a navigation system, and providing information of the selected registration point of interest on the object to a robotic arm system;

controlling movements of a robotic arm in the robotic arm system to drive a trackable element to move to the registration point of interest on the object by the robotic arm;

acquiring a force applied to a robotic arm terminal, the force detected by a force identification system; and determining whether the trackable element has moved to the registration point of interest on the object according to the force applied to the robotic arm terminal.

Optionally, the method for bone registration of a surgical robot further comprises:

acquiring a current position of the trackable element tracked by the navigation system;

determining whether the trackable element has moved to the registration point of interest on the object according to the current position of the trackable element.

Optionally, in the method for bone registration of a surgical robot, the step of determining whether the trackable element has moved to the registration point of interest on the object according to the force applied to the robotic arm terminal has a high priority, and the step of determining whether the trackable element has moved to the registration point of interest on the object according to the current position of the trackable element has a low priority.

Optionally, in the method for bone registration of a surgical robot, the step of determining whether the trackable element has moved to the registration point of interest on the object according to the force applied to the robotic arm terminal includes:

determining whether the force identification system operates normally, and if so, controlling the robotic arm to drive the trackable element to move towards the registration point of interest.

Optionally, in the method for bone registration of a surgical robot, after the step of controlling the robotic arm to drive the trackable element to move towards the registration point upon the determination of the force identification system operating normally, the method further includes:

comparing the force applied to the robotic arm terminal with a calibration value; and determining that the trackable element has moved to the registration point of interest on the object if the force applied to the robotic arm terminal is equal to or greater than the calibration value, or otherwise keeping controlling the robotic arm to drive the trackable element to move towards the registration point of interest until the force applied to the robotic arm terminal is equal to or greater than the calibration value.

Optionally, the method for bone registration of a surgical robot includes the following steps after determining that the trackable element has moved to the registration point of interest on the object:

determining whether the navigation system is able to track position of the trackable element normally; and if so, controlling the robotic arm to drive the trackable element to move to a next registration point of interest, or otherwise, controlling the robotic arm to adjust a pose of the trackable element until the navigation system is able to track position of the trackable element normally.

Optionally, the method for bone registration of a surgical robot includes the following step before controlling the robotic arm to move:

planning a movement trajectory by the robotic arm system based on the registration point of interest on the object selected by the navigation system, and driving the trackable element to move to the registration point of interest along the movement trajectory by the robotic arm.

Optionally, the method for bone registration of a surgical robot includes the following step before the step of determining whether the trackable element has moved to the registration point of interest on the object:

calculating a force applied to the robotic arm terminal according to forces applied to each robotic arm joints acquired by the force identification system;

acquiring a force applied to the robotic arm terminal by the force identification system;

comparing the calculated force applied to the robotic arm terminal with the acquired force applied to the robotic arm terminal; and updating the force identification system when a deviation between the calculated force applied to the robotic arm terminal and the acquired force applied to the robotic arm terminal is beyond a predetermined range.

Optionally, in the method for bone registration of a surgical robot, the forces applied to the respective robotic arm joints are acquired by:

detecting a force applied to each of the robotic arm joints by using a first sensor mounted thereon.

Optionally, in the method for bone registration of a surgical robot, the step of acquiring a force applied to the robotic arm terminal by the force identification system includes:

detecting a force applied to the robotic arm terminal by using a second sensor mounted at the robotic arm terminal.

Optionally, in the method for bone registration of a surgical robot, the force applied to the robotic arm terminal is calculated by a neural network calculation method and the method includes: before output of the calculated force applied to the robotic arm terminal, performing a neural network training on the force identification system and maintaining a network structure and a weight file after the neural network training.

According to another aspect of the present disclosure, there is also provided a surgical robot including a control system, a force identification system, a robotic arm system and a navigation system, the robotic arm system including a robotic arm with a robotic arm terminal configured to connect to a trackable element. The control system is communicatively connected with the force identification system, the robotic arm system and the navigation system, and the navigation system is communicatively connected with the robotic arm system.

The navigation system is configured to provide information of a registration point of interest on an object to the robotic arm system; and the robotic arm system is configured to control movements of the robotic arm to drive the trackable element to move to the registration point of interest on the object based on the information of the registration point of interest on the object.

The force identification system is mounted on the robotic arm and is configured to detect a force applied to the robotic arm terminal and provide the detected force applied to the robotic arm terminal to the control system, and the control system is configured to determine whether the trackable element has moved to the registration point of interest on the object according to the force applied to the robotic arm terminal.

Optionally, in the surgical robot, the navigation system is configured to acquire current position information of the trackable element and provide the current position information to the control system; and the control system is configured to determine whether the trackable element has moved to the registration point of interest on the object according to the current position information of the trackable element.

Optionally, in the surgical robot, the control system is configured such that determination of whether the trackable element has moved to the registration point of interest on the object according to the force applied to the robotic arm terminal has a high priority and determination of whether the trackable element has moved to the registration point of interest on the object according to the current position information of the trackable element has a low priority.

Optionally, in the surgical robot, the control system is configured to determine whether the force identification system operates normally, and if so, the control system controls the robotic arm to drive the trackable element to move towards the registration point.

Optionally, in the surgical robot, upon the determination of the force identification system operating normally, the control system is configured to compare the force applied to the robotic arm terminal with a calibration value pre-stored in the control system. If the force applied to the robotic arm terminal is equal to or greater than the calibration value, the control system determines that the trackable element have moved to the registration point of interest on the object. If the force applied to the robotic arm terminal is less than the calibration value, the control system keeps to control the robotic arm to drive the trackable element to move towards the registration point until the force applied to the robotic arm terminal is equal to or greater than the the calibration value.identification.

Optionally, in the surgical robot, after determination of the trackable element having moved to the registration point of interest on the object, the control system is further configured to determine whether the navigation subsystem is able to track position of the trackable element normally. If so, the control system controls the robotic arm to drive the trackable element to move to a next registration point of interest. Or otherwise, the control system controls the robotic arm to adjust a pose of the trackable element until the navigation subsystem is able to track the position of the trackable element normally.

Optionally, in the surgical robot, the robotic arm comprises a plurality of robotic arm joints, and the force identification system comprises a first force identification device and a second force identification device;

Optionally, the first force identification device comprises a plurality of first sensors, and each of the robotic arm joints is provided with at least one of the first sensors, where each first sensor is configured to detect a force applied to a corresponding robotic arm joint of the robotic arm joints.identification Optionally, the second force identification device comprises at least one second sensor mounted at the robotic arm terminal, the second sensor configured to detect a force applied to the robotic arm terminal;

Optionally, the control system is configured to:

calculate a force applied to the robotic arm terminal according to forces applied to respective robotic arm joints detected by the plurality of first sensors; compare the calculated force applied to the robotic arm terminal with the detected force applied to the robotic arm terminal; and update the force identification system when a deviation between the calculated force applied to the robotic arm terminal and the detected force applied to the robotic arm terminal is beyond a predetermined range.

Optionally, in the surgical robot, the first sensor comprises at least one selected from the group consisting of a dual encoder, a torque sensor and a distributed grating sensor, and the second sensor comprises a six-axis sensor.

Optionally, in the surgical robot, each of the plurality of robotic arm joints has a dual encoder mounted thereon, the dual encoder comprising an absolute encoder and an incremental encoder. The robotic arm further comprises, a driver and a reducer for driving at least one of the robotic arm joint, an output of the driver coupled to an input of the reducer, an output of the reducer coupled to the robotic arm joint. One of the absolute encoder and the incremental encoder is provided at the input of the reducer and the other one of the absolute encoder and the incremental encoder is provided at the output of the reducer.

Optionally, in the surgical robot, a force $\tau$ applied to the robotic arm joint is calculated according to:

$$\tau = K\delta$$
$$\delta = \frac{T1}{c1} - \left(\frac{T2}{c2} + S0\right)$$

where K is a stiffness coefficient of the reducer; $\delta$ is a deformation amount of the robotic arm joint; T1 is an absolute position of the robotic arm joint fed back by the absolute encoder; T2 is a relative position of the robotic arm joint fed back by the incremental encoder; c1 is a resolution of the absolute encoder; c2 is a resolution of the incremental encoder; S0 is a startup initialization position of the incremental encoder.

Optionally, in the surgical robot, the dual encoder is communicatively connected with the control system; and the control system is configured to obtain a force applied to the robotic arm joint according to a relationship between a data deviation of the dual encoder and the force applied to the robotic arm joint.

Optionally, in the surgical robot, the control system is configured to calculate a force applied to the robotic arm terminal by using a neural network calculation method, and perform a neural network training on the force identification system and maintain a network structure and a weight file after the neural network training, before outputting the calculated force applied to the robotic arm terminal identification.

Optionally, in the surgical robot, the surgical robot comprises an automatic operation mode and an auxiliary operation mode;

when the surgical robot is in the automatic operation mode, the robotic arm subsystem plans a movement trajectory according to a received information of a registration point of interest, and controls the robotic arm to drive the trackable element to move to the registration point of interest on the object along the movement trajectory;

when the surgical robot is in the auxiliary operation mode, the robotic arm is driven by an external force to move the trackable element to the registration point of interest on the object.

In the method for bone registration of a surgical robot and the surgical robot provided in the present disclosure, the use of a surgical robot for bone registration is able to improve the efficiency of bone registration, help the operator in reducing workload, and in particular, to identify information of the force applied to the robotic arm terminal through the force identification system to facilitate determination of situation of the trackable element puncturing into the cartilage, so as to control the insertion depth into cartilage, ensure accurate selection of the registration point on the bone, improving the accuracy and safety of bone registration. Further, various sensors of the force identification system are adopted to obtain information of the forces applied to the robotic arm terminal respectively, which helps the mutual verification of the forces applied to the robotic arm terminal, thereby enabling to ensure the accuracy and reliability of the force detection. Moreover, in the bone registration process, it further determines whether the force identification system operates normally, and performs the bone registration by hand when the force identification system operates abnormally, which enables to further ensure the accuracy and reliability of the force detection. Furthermore, the force applied to the robotic arm terminal can also be obtained according to the network calculation method, which enables to further improve the precision of the force detection.

BRIEF DESCRIPTION OF THE DRAWINGS

Features, properties, and advantages of implementation methods and related embodiments will be described with reference to the accompanying figures. In the figures.

DETAILED DESCRIPTION

Embodiments of the present disclosure will de clearly and thoroughly described below with reference to the accompanying drawings. Obviously, the described embodiments are only a part of the embodiments of the present disclosure, but not all of them. Based on embodiments of the present disclosure, all other embodiments obtained by a person of ordinary skilled in the art without creative efforts shall fall within the protection scope of the present disclosure.

As used in present disclosure, the meaning of "a," "an," and "the" include singular and plural references, unless the context clearly dictates otherwise. As used in present disclosure, the term "or" generally includes the meaning of "and/or", unless the context clearly dictates otherwise. As used in present disclosure, the term "some", "several", "a number of" includes the meaning of "at least one", unless the context clearly dictates otherwise. As used in present disclosure, the term "at least two" generally includes the meaning of "equal to or greater than two", unless the context clearly dictates otherwise. In addition, the term "first", "second", "third" are used only for the purpose of description and should not be understood as an indication or hint of relative importance or as an implicit indication of the number of technical features indicated. Therefore, the features defined as "first", "second", and "third" may explicitly or implicitly include one or at least two of the said features.

The core idea of the present disclosure is to provide a surgical robot, which aims to complete the bone registration process through the collaborative operation of the surgical robot, and obtain information of the force (includes the force and the torque) applied to the robotic arm terminal with the aid of the force identification system to ensure that the trackable element is able to accurately select the registration point of interest on the bone, improving the accuracy and safety of bone registration. Besides, no damage would occur when a sensor used in the present disclosure receive an excessive external force, ensuring the use reliability of the sensor. In particular, the sensors are also able to verify each other to further ensure the accuracy and reliability of bone registration.

Figure 1:
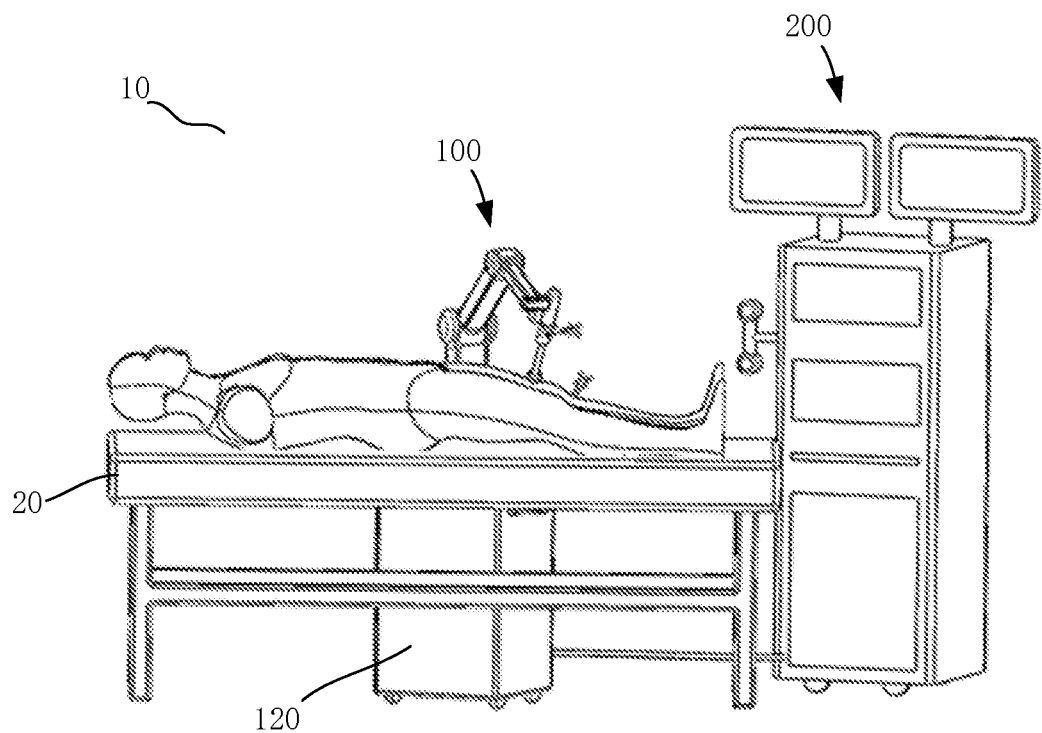
FIG. 1 is an overall schematic diagram of a surgical robot performing an operation according to an embodiment of the present disclosure.

FIG. 1 is an overall schematic diagram of a surgical robot 10 of this embodiment performing a knee surgery. As shown in FIG. 1, this embodiment provides a surgical robot 10 including a robotic arm system 100 and a navigation system 200 communicated with the robotic arm system 100. In this embodiment, the robotic arm system 100 has an automatic operation mode and an auxiliary operation mode. When the robotic arm system 100 is in the automatic operation mode, the surgical robot 10 completes the bone registration process automatically; and when the robotic arm system 100 is in the auxiliary operation mode, the surgical robot 10 assists the operator to complete the bone registration process. The navigation system 200 is used for pre-operative operation planning and intra-operative navigation, and is able to track the instruments at the robotic arm terminal during the operation and display images of the the instrument positions in real time before and during the operation to make the operator know the relationship between the the instrument position and the target object at any time, enabling a more accurate operation of the operator. Therefore, the navigation system 200 is the visual identification part of the surgical robot 10.

Figure 2:
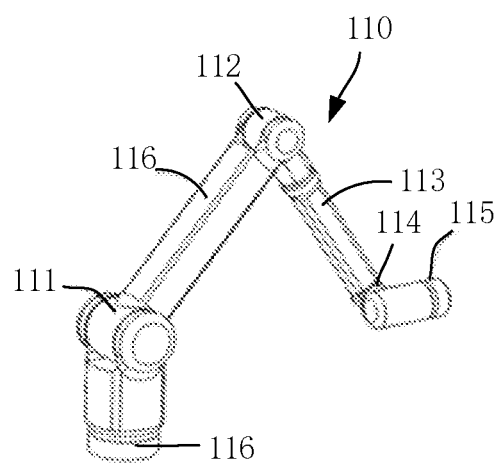
FIG. 2 is a structural schematic diagram of a robotic arm according to an embodiment of the present disclosure.

FIG. 2 is a structural schematic diagram of a robotic arm 110 in this embodiment. As shown in FIG. 2, the robotic arm system 100 includes a robotic arm 110. The robotic arm 110 includes a number of robotic arm joints connected in sequence and a robotic arm terminal. The robotic arm joint, for example, is a rotary joint and is configured to control the position and posture of the surgical instrument driven by the robotic arm terminal. In this embodiment, the robotic arm 110 includes at least five rotary rotary joints connected in sequence to achieve at least five degrees of freedom. Further, any adjacent rotary joints are connected through a connecting arm.

Referring to the robotic arm 110 shown in FIG. 2, the robotic arm 110 has five degrees of freedom, and includes a first rotary joint 111, a second rotary joint 112, a autorotation joint 113, a third rotary joint 114, and a fourth rotary joint 115 sequentially connected. Moreover, the rotation axis of the first rotary joint 111, the rotation axis of the second rotary joint 112, and the rotation axis of the third rotary joint 114 are parallel to each other, and the rotation axis of the third rotary joint 114 and the axis of the fourth rotary joint 115 are perpendicular to each other. Further, any adjacent rotary joints are connected by a connecting arm 116. The first rotary joint 111 is connected to a connecting arm 116. One end of the connecting arm 116 is connected to the first rotary joint 111, with the other end fixedly connected to a base. The base can be fixed to the sickbed 20 or the surgical cart 120. The fourth rotary joint 115 is connected to a surgical instrument. In this embodiment, the surgical tool is a trackable element, so that the trackable element is connected through the robotic arm 110. Moreover, the trackable element is driven by the robotic arm to move and select the registration points of interest on the patient's bone to complete the bone registration.

Further, the surgical robot 10 further includes a force identification system or a force sensor. The force identification system is disposed on the robotic arm 110 for detection of the force applied to the robotic arm terminal. The force applied to the robotic arm terminal is the force applied to the trackable element in the process of cartilage puncture. In practical application, it is convenient to determine whether the trackable element has punctured to the surface of the bone according to the force applied on the robotic arm terminal, and in this way, it is convenient to accurately control the insertion depth of the trackable element into the cartilage, so as to correctly select the registration point on the bone and improve the accuracy and safety of bone registration.

In this embodiment, the surgical robot 10 further includes a control system, which is communicatively connected with the force identification system, the robotic arm system 100 and the navigation system 200. The force identification system detects and feeds back information of the force applied to the robotic arm terminal to the control system, and the control system determines whether the trackable element has punctured to the bone surface, that is, determine whether the trackable element has moved to the registration point of interest on the bone, according to the information of the force applied to the robotic arm terminal. Further, A calibration value of the force applied to the robotic arm terminal is stored in the control system and is calibrated through experiments. The control system compares the detected force applied to the robotic arm terminal with the calibration value. If the actual detected force matches the calibration value (referring that the actual detected force reaches the calibration value, i.e., being greater than or equal to the calibration value), the control system determines that the trackable element has punctured to the surface of the bone and has correctly selected the registration point of interest. Otherwise, if the actual detected force not reaches the calibration value (i.e., being less than the calibration value), the control system keeps to control the robotic arm to drive the trackable element to move towards the registration point (i.e., continuing to go deep into) and repeatedly compares the detected force applied to the robotic arm terminal with the calibration value until the force applied to the robotic arm terminal is equal to or greater than the the calibration value.

Further, the force identification system includes a first force identification device and/or a second force identification device. The first force identification device comprises a plurality of first sensors, and each of the robotic arm joints is provided with at least one of the first sensors. Each of the first sensors is configured to detect the force applied to the rotary joint. Further, the control system calculates the force applied to the robotic arm terminal according to information of forces of all robotic arm joints fed back by the first force identification device. Here, the control system may calculate the force applied to the robotic arm terminal according to a known method in the art. In addition, the control system can use any existing PLC controller, single chip microcomputer, microprocessor, and FPGA, the selection of which is known to the skilled in the art based on the present disclosure and the general knowledge in the field. The second force identification device includes at least one second sensor, and the second sensor is disposed on the robotic arm terminal, for example, on the fourth rotary joint 115 of the robotic arm to directly detect the force applied to the robotic arm terminal. Compared with the first force identification device, the second force identification device can directly obtain the force applied to the robotic arm terminal without calculation, which results in a more simple and convenient use and a higher accuracy. In this embodiment, the force applied to the robotic arm includes force and torque.

Further, the first force identification device includes at least one of a position sensing device, a pressure sensing device, and a grating sensing device. Of course, two or more sensing devices may be used in combination. The position sensing device includes an absolute position sensing device and a relative position sensor device. The absolute position sensing device includes an absolute encoder, such as an optical encoder, an absolute magnetic encoder, an absolute rotary transformer encoder or a absolute rotary potentiometer, or the like. Accordingly, the relative position sensing device includes an incremental encoder. The pressure sensing device includes a pressure sensor. The grating sensing device includes a distributed grating sensor. That is, the first force identification device includes one or more types of first sensors. Further, types of the first sensors arranged at each rotary joint of the robotic arm 110 may be the same or different. For example, pressure sensors are provided on some rotary joints, and dual encoders are provided on other rotary joints. Preferably, both the dual encoders and the pressure sensors are provided on a same rotary joint. For example, a rotary joint is provided with a dual encoder, a pressure sensor, a grating sensor or any combination thereof. Further, the second force identification device preferably includes a six-axis sensor, and one or more of the six-axis sensor is provided.

Figure 3:
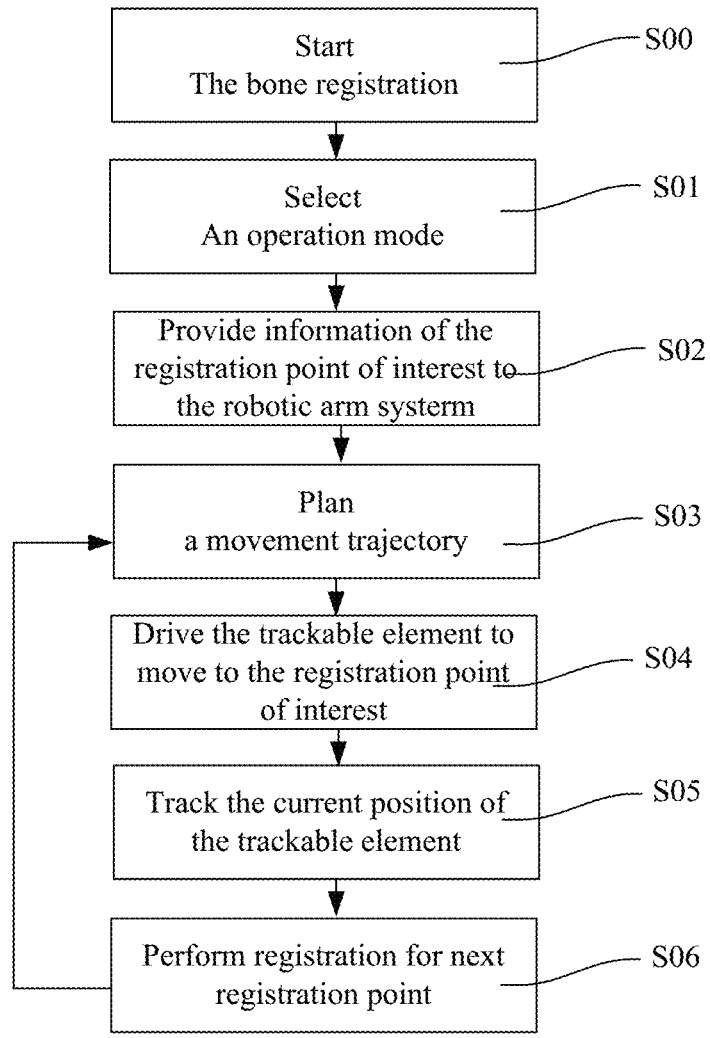
FIG. 3 is a general flowchart of a bone registration performed by a surgical robot according to an embodiment of the present disclosure.

FIG. 3 is a general flowchart of a bone registration performed by the surgical robot 10 in this embodiment. As shown in FIG. 3, the bone registration process performed by the surgical robot 10 includes the following steps: entering into a bone registration mode first and starting with the bone registration S00; and then, performing the following steps:

Step S01: selecting an operation mode of the bone registration, for example, selecting a mode in which a surgical robot automatically completes the bone registration, or a mode in which a surgical robot assists in completing the bone registration.

Step S02: providing, by the navigation system, information of the registration point of interest to the robotic arm system 100 after designation of the operation mode. Specifically, in the pre-operative planning, the navigation system 200 selects the registration point of interest based on the preoperatively collected image information, patient information, prosthesis information, or feature points selected by the operator, and provides information of the selected registration point of interest to the robotic arm system. More specifically, the navigation system 200 reconstructs a three-dimensional bone model according to the CT registration results, in which the algorithm used may be a multi-level reconstruction method or a maximum intensity projection reconstruction method, and selects registration point of interest about the feature point based on the selected feature point by the operator. After selecting the registration point of interest, the navigation system 200 provides the base coordinates of the registration point of interest in space relative to the surgical robot to the robotic arm system 100, that is, the navigation system 200 provides position information of the registration point of interest to the robotic arm system 100.

Step S03: planning, by the robotic arm system 100, a movement trajectory to drive the robotic arm terminal to move to a registration point of interest along a predetermined movement trajectory, after receiving the position information of the registration point of interest. When planning a movement trajectory, the robotic arm 110 connects the trackable element and performs a trajectory planning according to the position of the registration point of interest. During the planning process, the robotic arm system 100 uses the robotic forward and inverse kinematic equations and dynamic equations to complete the trajectory planning.

Step S04: driving, by the robotic arm 110, the trackable element to move to the registration point of interest and select the registration point on bone according to the selected operation mode of bone registration, after planning the movement trajectory. Here, the control system controls the robotic arm 110 to drive the trackable element to the registration point of interest in the automatic operation mode. In the auxiliary operation mode, the operator operates the robotic arm 110 and drives the trackable element to move to the registration point of interest under the guidance of the robotic arm.

When the trackable element has moved to the registration point of interest, step S05 is executed. In step S05, the navigation system 20 tracks the current position of the trackable element, and the control system determines whether the trackable element has moved to the registration point of interest according to the current position of the trackable element. If the trackable element has moved to the registration point of interest, the control system determines that registration of this registration point has completed, and controls to perform registration for next registration point S06 and repeatedly perform steps S03 to S05 until all the registration points of interest has been registered.

In particular, when determining whether the trackable element has moved to the registration point of interest, the control system also determines whether the trackable element has punctured through the cartilage and reached the bone surface according to the force applied to the robotic arm terminal. If the trackable element has punctured through the cartilage and reached the bone surface, the control system confirms that the trackable element has moved to the registration point of interest and has correctly selected the registration point on the bone. In some embodiments, the control system determines whether the trackable element has moved to the registration point of interest according to a combination of the current position of the trackable element and the force applied to the robotic arm terminal. Further, the control system prefers to determine whether the trackable element has moved to the registration point of interest according to the force applied to the robotic arm terminal. Specifically, although the trackable element has not moved to the target position, if the force applied to the robotic arm terminal is equal to or greater than the calibration value, the control system confirms that the trackable element has moved to the registration point of interest. Further, if the trackable element has moved to the target position while the force applied to the robotic arm terminal is less than the calibration value, it is preferred that the operator determines whether to continue the puncture to the bone surface. Therefore, the step of determining whether the trackable element has moved to the registration point of interest according to the force applied to the robotic arm terminal has a high priority and the step of determining whether the trackable element has moved to the registration point of interest according to the current position of the trackable element has a low priority.

Figure 4:
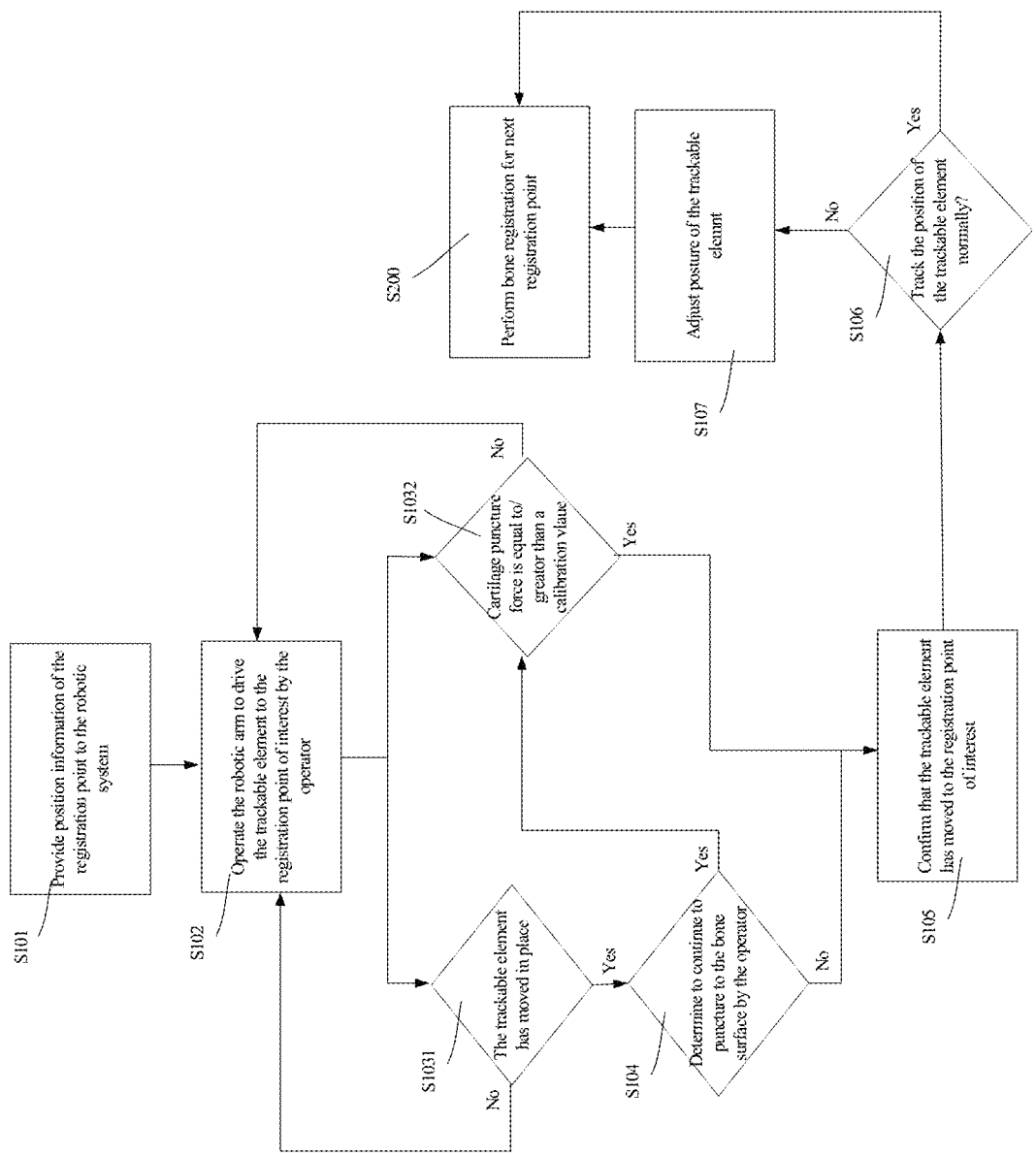
FIG. 4 is a flowchart of a bone registration performed by a surgical robot in a auxiliary operation mode according to an embodiment of the present disclosure.

FIG. 4 is a flowchart of a bone registration in the auxiliary operation mode according to a preferred embodiment. As shown in FIG. 4, if the auxiliary operation mode is selected in the above step S01, the surgical robot 10 performs the following steps.

Step S101: providing, by the navigation system 200, position information of the registration point of interest to the robotic arm system 100.

Step S102: operating, by the operator, the robotic arm 110 to drive the trackable element to move to the registration point of interest under guidance of the robotic arm 110, after receipt of the position information of the registration point of interest. That is, the operator controls the robotic arm 110 to drive the trackable element to puncture to the cartilage until it reaches the bone surface, and select the registration point on bone. During this process, the robotic arm system 100 may guide the operator to operate the robotic arm 110 by a well known method in the art, such as an impedance control method.

After the trackable element has moved to the registration point of interest, step S1031 is executed: the control system determines whether the trackable element has moved in place according to the current position information of the trackable element acquired by the navigation system 200:

If so, step S104 is preferably performed: the operator intervenes and further determines whether to continue to puncture to the bone surface; Otherwise, proceed to perform step S102.

While performing step S1031, it is also preferable to perform step S1032: the control system determines whether the cartilage puncture force is equal to or greater than the calibration value according to the the force applied to the robotic arm terminal:

If so, the control system confirms that the trackable element has moved to the registration point of interest, and the result of step S105 is obtained;

Otherwise, proceed to perform step S102.

Further, when step S104 is performed, if the operator considers that the puncture to the bone surface needs to be continued, step S1032 is selected to perform; otherwise, if the operator considers that it is unnecessary to continue to puncture to the bone surface, the result of step S105 can be directly obtained. The reason for the above is that there may be a slight difference between the actual patient's bone and the resulted image from CT reconstruction, which may cause the actual bone surface to be inconsistent with the surface of the 3D model reconstructed by CT. If only the force identification system is used to determine whether the bone surface has reached, there may exist a certain risk. Therefore, it is necessary to further rely on the operator's artificial judgment to reduce the risk of inaccurate registration point selection, further ensuring the accuracy of bone registration.

Further, after obtaining the result of step S105, proceed to perform step S106: determining whether the navigation system 200 is able to normally track the position of the trackable element:

If so, go to step 200: driving the trackable element to move and perform registration of the next registration point;

Otherwise, perform step S107: operating, by the operator, the the robotic arm to adjust posture of the trackable element with the guidance of the robotic arm, until the navigation system 200 is able to track the position of the trackable element.

Figure 5:
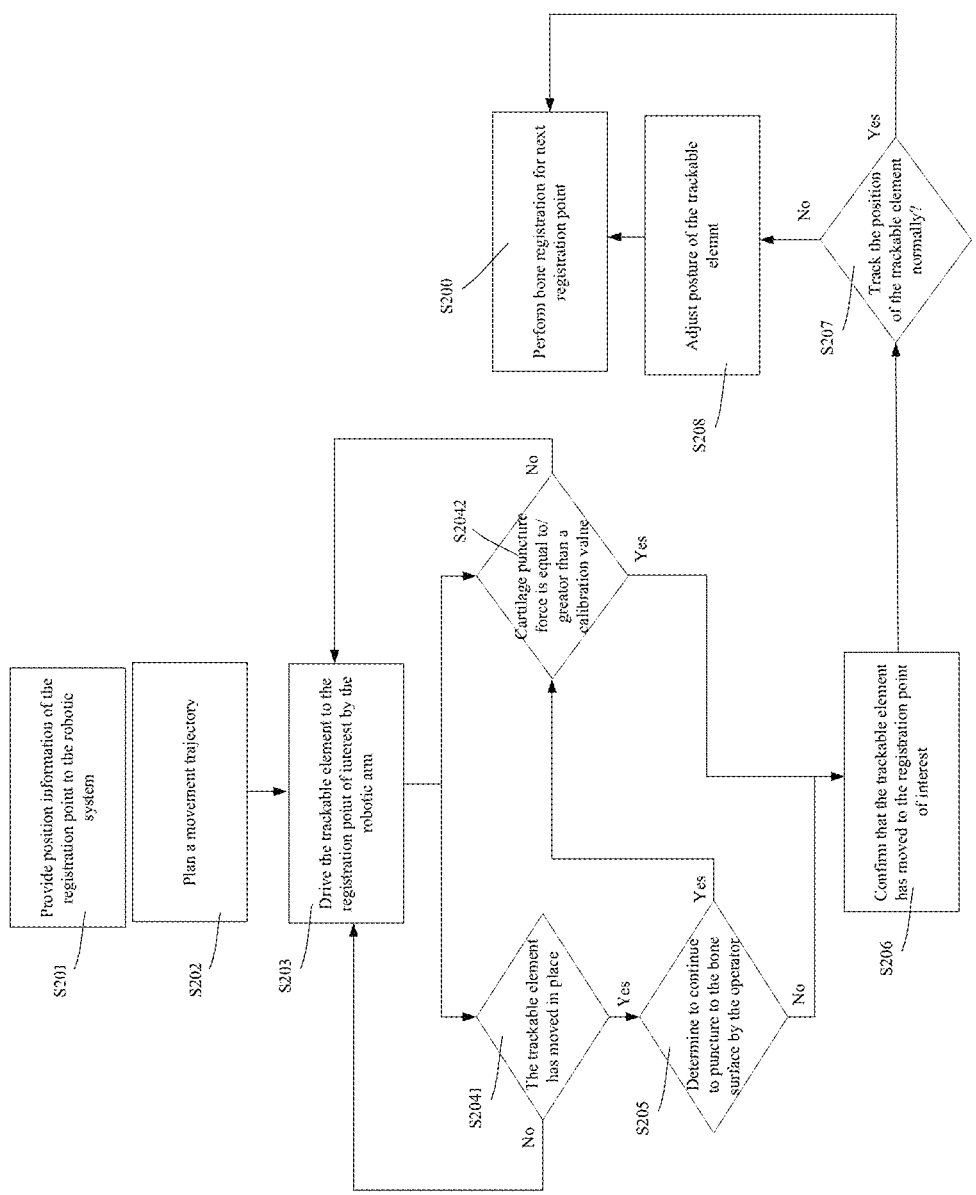
FIG. 5 a flowchart of a bone registration performed by a surgical robot in a automatic operation mode according to an embodiment of the present disclosure.

FIG. 5 is a flowchart of a bone registration in the automatic operation mode according to a preferred embodiment. As shown in FIG. 5, if the automatic operation mode is selected in the above step S01, the surgical robot 10 performs the following steps:

Step S201: providing, by the navigation system 200, position information of the registration point of interest to the robotic arm system 100.

Step S202: planning, by the robotic arm system 100, a movement trajectory after receipt of the position information of the registration point of interest.

Step S203: controlling, by the control system, the robotic arm 110 to drive the trackable element to move to the registration point of interest along the movement trajectory after the movement trajectory planning That is, the trackable element punctures the cartilage until it reaches the bone surface under the driving of the robotic arm, and selects the registration point on the bone.

After the trackable element has moved to the registration point of interest, step S2041 is executed: determining, by the control system, whether the trackable element has moved in place according to the current position information of the trackable element acquired by the navigation system 200:

If so, step S205 is preferably performed: intervening and further determining, by the the operator, whether to continue to puncture to the bone surface;

Otherwise, proceed to perform step S203.

Preferably, when step S2041 is performed, step S2042 is also performed: determining, by the control system, whether the cartilage puncture force is equal to or greater than the calibration value according to the force applied to the robotic arm terminal.

If so, the control system directly confirms that the trackable element has moved to the registration point of interest, i.e., the result of step S206 is obtained;

Otherwise, step S203 is continued.

Further, in performing step S205, if the operator considers that it is necessary to continue to puncture to the bone surface, step S2042 is preferably performed; otherwise, if the operator considers that it is not necessary to continue to puncture to the bone surface, the result of step S206 can be obtained.

Further, after obtaining the result of step S206, the robotic arm system 100 sends a completion signal to the navigation system 200, and the navigation system 200 tracks or collects the position of the trackable element according to the completion signal and performs step S207: determining whether the navigation system 200 is able to track or collect the position of the trackable element normally:

If so, go to step S200: driving the trackable element to move and perform registration for the next registration point;

Otherwise, perform step S208: controlling, by the control system, the movement of the robotic arm to adjust the posture of the trackable element until the navigation system 200 is able to track the position of the trackable element.

Specifically, when the position of the trackable element is beyond the field of view of the navigation system 200, the robotic arm 110 drives the trackable element to perform a rotary movement with an unchanged spatial position, that is, the spatial position of the trackable element is not changed and only the posture of the trackable element is changed. At this time, a part of the rotary joints of the robotic arm remains stationary, and the other part of the rotary joints drives the trackable element to rotate around an active remote-center-of-motion point. The robotic arm stops moving until the navigation system 200 is able to normally track or collect the position of the trackable element. In this way, bone registration at a registration point is successively performed. In the auxiliary operation mode, the robotic arm can guide the operator to hold the trackable element to rotate around the active remote-center-of-motion point, and adjust the pose of the trackable element.

Figure 6A:
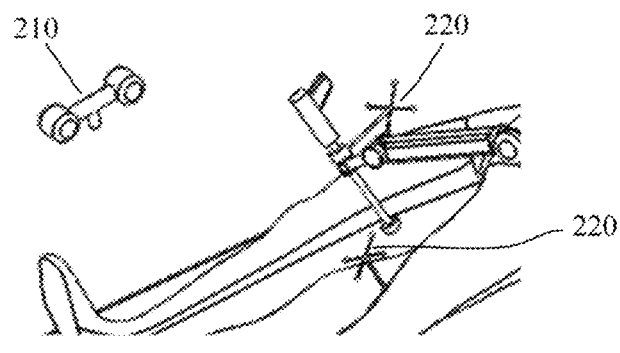
FIG. 6a is a schematic diagram of a trackable element outside the field of view of the navigation system according to an embodiment of the present disclosure.
Figure 6B:
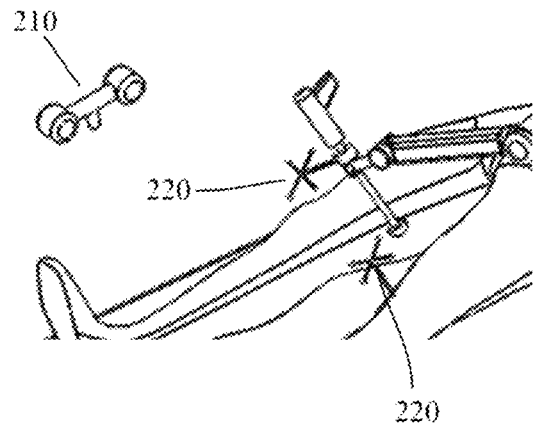
FIG. 6b is a schematic diagram of a trackable element inside the field of view of the navigation system according to an embodiment of the present disclosure.

As shown in FIG. 6a and FIG. 6b, the navigation system 200 includes a camera 210 and an optical target 220. The camera 210 is, for example, a binocular camera. One optical target 220 is mounted on the trackable element, and another optical target 220 is mounted and immobilized on the patient's bone. For example, when the optical target 220 on the trackable element is beyond the field of view of the camera 210 as shown in FIG. 6a, the posture of the trackable element can be changed to make the optical target 220 rotate around the active remote-center-of-motion point and thus enter into the field of view of the camera 210, as shown in FIG. 6b.

Figure 7:
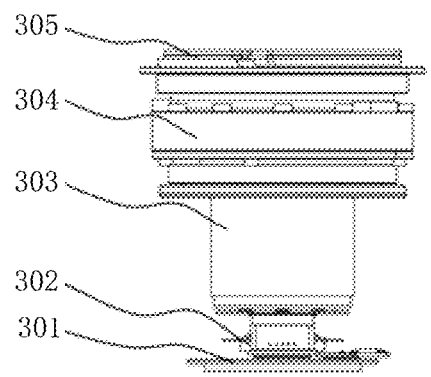
FIG. 7 is a schematic diagram of a joint module according to an embodiment of the present disclosure.
Figure 8:
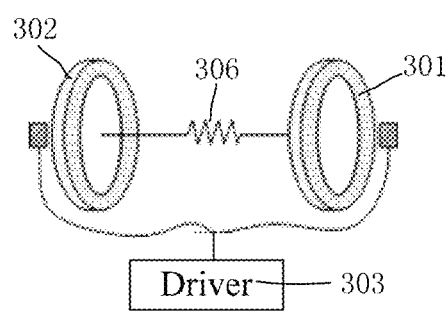
FIG. 8 shows a principle of a joint torque detection by a dual encoder according to an embodiment of the present disclosure.

In this embodiment, the position sensing device includes two encoders (or dual encoders), which are an absolute encoder 301 and an incremental encoder 302. Taking the torque detection of a rotary joint as an example, as shown in FIG. 7 and FIG. 8, a driver 303 and a speed reducer 304 are mounted on the rotary joint, the output of the speed reducer 304 connected to the rotary joint, the input of the speed reducer 304 connected to the driver 303 which drives the rotary joint to rotate through the speed reducer 304. The driver 303 includes a driving motor. One of the absolute encoder 301 and the incremental encoder 302 is mounted at the output of the driving motor, and the other one of the absolute encoder 301 and the incremental encoder 302 is disposed at the output of the reducer 304 (such as the output shaft of the rotary joint). The absolute encoder 301 collects the absolute state parameter T1 of the rotary joint in real time, and the incremental encoder 302 collects the relative state parameter T2 of the rotary joint in real time. Both the absolute state parameter T1 and the relative state parameter T2 are sent to the control system.

When the rotary joint is subjected to an external force, the output torque of the driving motor τ equals to the moment τ' of the external force applied to the rotary joint according to the principle of torque balance, while the output torque of the driving motor τ relates to the deformation amount of the rotary joint:

$$\tau = K\delta$$

where K is a stiffness coefficient of the reducer 304, such as the stiffness coefficient of the harmonic reducer; δ is a deformation amount of the robotic arm joint.

In this embodiment, there is a corresponding relationship between the deformation amount of the rotational joint and the absolute state parameter T1 and the relative state parameter T2, and the corresponding relationship can be calibrated in advance through experiments. Or, the deformation amount of the rotational joint can be calculated by the following formula:

$$\delta = \frac{T1}{c1} - \left(\frac{T2}{c2} + S0\right)$$

where T1 is an absolute position of the robotic arm joint fed back by the absolute encoder, the absolute position for example being the absolute rotation angle; T2 is a relative position of the robotic arm joint fed back by the incremental encoder, the relative position for example being the relative rotation angle; c1 is a resolution of the absolute encoder; c2 is a resolution of the incremental encoder; S0 is a startup initialization position of the incremental encoder.

Therefore, the control system is able to obtain the output torque τ of the driving motor based on the deformation amount of the rotary joint and the stiffness coefficient of the reducer, and thus determines the external force torque τ' on the rotating joint according to the output torque of the driving motor.

In an alternative embodiment, as shown in FIG. 8, two encoders are mounted at the input of the reducer 304 and the output of the reducer, respectively. Theoretically, the reducer and other transmission elements can be equivalent to an elastic body 306. When the rotating joint is subjected to an external force, the equivalent elastic body 306 in the middle of the two encoders will deform, resulting in a deviation between the datas collected by the two encoders, and this deviation relates to the external force. Therefore, the relationship between the reading deviation of the two encoders and the external force can be obtained through the test calibration. The the driver in utilized to obtain the readings of the two encoders, and the readings are then uploaded to the control system. The control system obtains the deviation values of the two encoders according to the readings, and then obtains the external force applied to the joint according to the deviation values.

For the convenience of description, the driver, reducer, rotary joint and the first force identification device are collectively called as a joint module in this disclosure. In addition to the position sensing device, the joint module can also include at least one torque sensor 305 that is an optical-mechanical deformation type, an electromagnetic induction type, or a resistance strain type. As shown in FIG. 7, the torque sensor 305 directly detects information of the torque applied to the rotary joint. Here, the position sensing device and the torque sensor can be mutually checked to monitor the work status of the two, thereby further improving the accuracy of the torque identification of the rotary joint. The torque sensor 305 may be mounted on the output of the reducer, such as on the output shaft of the joint. Further, the output current of the driving motor can also be collected, so that the control system can obtain information of the external force applied to the rotary joint according to the output current of the driving motor to achieve the redundant detection.

Further, the torque sensor 305 is a pressure sensor. Before leaving the factory, the zero point calibration of the pressure sensor can be performed. Specifically, an external force is applied to the rotary joint of the robotic arm and the output data of the pressure sensor is read, so that the zero point calibration of the pressure sensor can be performed according to the measured output data. In practical use, when a rotary joint of the robotic arm is subjected to an external force, the deformation amount of the pressure sensor is converted into an electrical signal that is transmitted to the control system. The control system is able to calculate the external force applied to the rotary joint based on the electrical signal of the pressure sensor.

In an alternative embodiment, the torque sensor 305 may also be a distributed grating sensor. The distributed grating sensor is arranged at the rotary joint and can be connected with the housing of the robotic arm. The grating sensor includes a fiber bragg grating strain gauge to form a strain bridge. The arrangement of the strain bridge can refer to the existing arrangement of the resistor strain bridge. In addition, a fiber bragg grating strain gauge is provided at each rotating joint, and the fiber bragg grating strain gauges of respective joint modules share one fiber channel More specifically, the modulated light is emitted by a broadband light source placed at the rear end (such as the base) of the robotic arm, and is reflected after passing through the fiber bragg grating strain gauges of respective joint modules. The control system performs the demodulation to calculate the wavelength of the reflected light. If the rotary joint is subjected to an external force, the wavelength of the reflected light will change. Since the amount of wavelength change is proportional to the strain of the distributed grating sensor, the strain of each distributed grating sensor can be measured. The control system is able to calculate the external force applied to each joint module according to the corresponding strain of the distributed grating sensor.

It should be known that the force identification system can further verify the accuracy of the torque information in addition to identify the torque of the rotary joint and/or the torque of the robotic terminal. That is, the force identification system preferably includes a first force identification device and a second force identification device, in which the first force identification device may include a plurality of first sensors to detect torque information in different ways. For example, the second force identification device directly senses the torque information of the robotic arm terminal through a six-axis sensor, and the first force identification device can sense the torque applied to a rotary joint through one or more of the dual encoder, pressure sensor, and grating sensor. The first force identification device can also obtain information of the torque applied to a joint by detecting the output current of the driving motor. Therefore, during the bone registration process, information of the force applied to the robotic arm terminal can be obtained through a variety of detection methods, and the detected information are verified to determine whether the torque information used in the calculation is accurate. In addition, detection of the torque applied to a the rotary joint can also protect the joint module. For example, the robotic arm has an active adjustment mode and/or a passive adjustment mode. Generally, the operation mode that the power mechanism such as the driving motor on the robotic arm 110 drives the robotic arm to move is the the active adjustment mode of the robotic arm. In contrast, the operation mode that the Cartesian force drives a robotic arm to move is the passive adjustment mode of the robotic arm.

In the active adjustment mode, the control system, after obtaining the torque of each rotary joint on the robotic arm, controls the driving motors of all the rotary joints whose torque is greater than the predetermined calibration value (that is, the driving motor of the joint having a drive torque greater than the predetermined calibration value, similarly hereinafter) to stop output. The calibration value is, for example, zero. In this way, pose adjustments of the robotic arm caused by human misoperation during the operation of the robotic arm in the active adjustment mode is able to be avoided, thereby allowing to enhance safety and reliability during the use of the robotic arm. In the passive adjustment mode, after obtaining the torque of each robotic arm joint, the control system further controls driving motors of all the rotary joints whose torque is greater than the preterminal calibration value (the calibration value is, for example, zero) to output. In this way, the driving motor of the rotating joint of the robotic arm with a torque greater than the predetermined calibration value can cooperate with the operator to drive the rotary joint of the robotic arm to move, so as to enable the operator to overcome the resistance of the rotary joint on the robotic arm, thereby enabling the control system to assist the operator in moving the robotic arm to the predetermined position. In this manner, the comfort and convenience of the passive adjustment operation of the robotic arm is improved. Obviously, from the beginning to the ending of the external force applied to the robotic arm, the driving motors of the rotary joints whose torque is greater than the predetermined calibration value (the calibration value is, for example, zero) output power, so that passive adjustments of the robotic arm by the operator are able to save more power and become more simple and convenient.

Taking a six-axis sensor mounted on the rotary joint of the robotic arm terminal and dual encoders mounted at respective joint modules as an example, each force identification device provides the obtained torque information to the control system, and the control system then compares the force applied to the robotic arm terminal calculated by the dual encoder with the force applied to the robotic arm terminal directly obtained by the six-axis sensor, that is, the control system verifies the received torque information and determines whether to update the calibration parameters based on the calibration results, and also implements corresponding safety precautions based on the calibration results at the same time. For example, the stiffness coefficient K of the reducer in the dual encoder or related parameters of the pressure sensors and the grating sensors are updated using the six-axis sensor as a calibration reference.

Further, the control system is also configured to determine whether the torque sensor exceeds the range of the torque sensor according to the received torque information, to protect the torque sensor, which further ensure the accuracy of the torque information of each joint during the bone registration process, thereby further enhancing accuracy of the determination of the cartilage puncture force to ensure the accuracy of bone registration.

Figure 9:
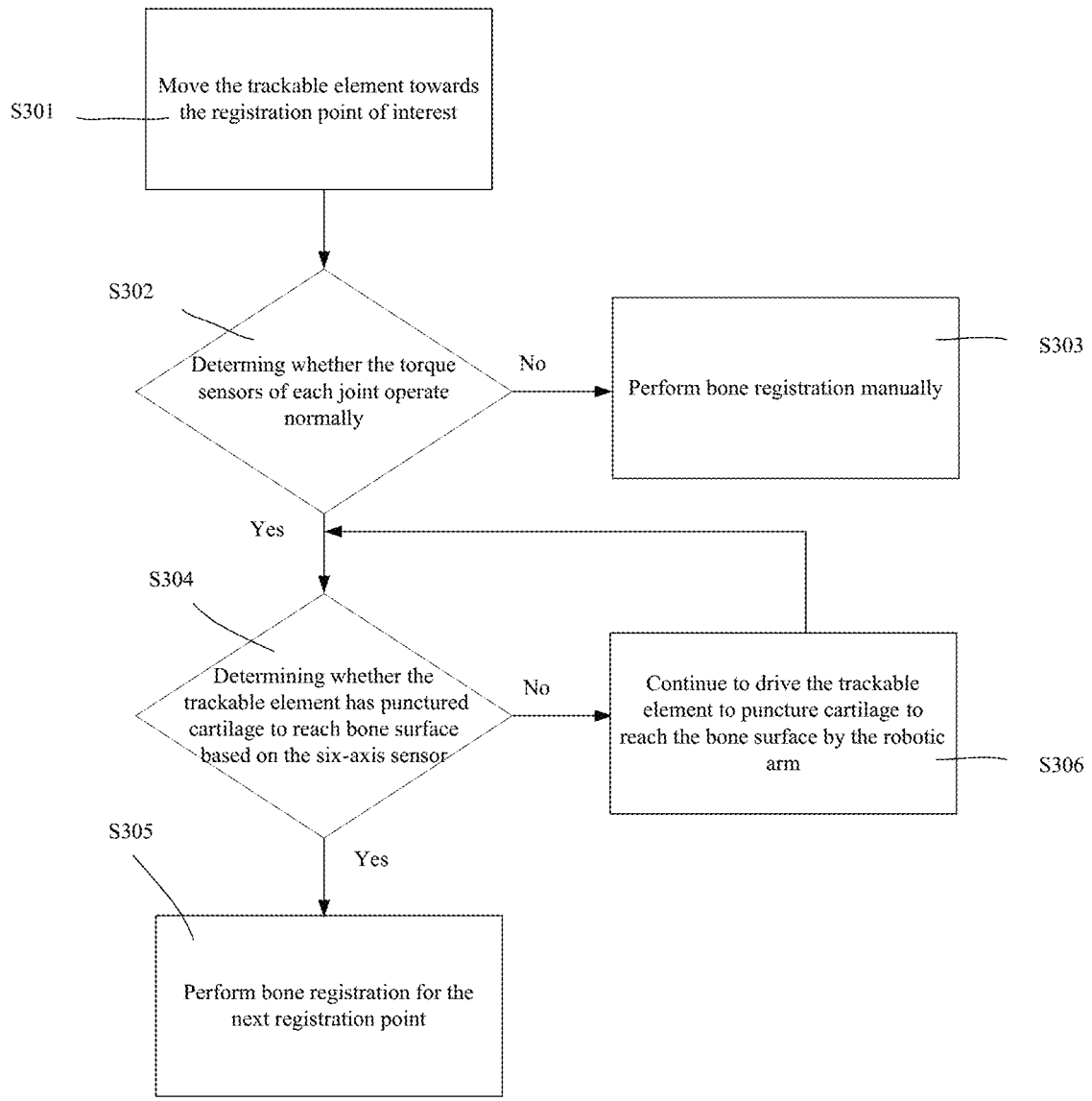
FIG. 9 is a flowchart of a protection for a joint module according to an embodiment of the present disclosure.

FIG. 9 is a flowchart of the bone registration according to a preferred embodiment. As shown in FIG. 9, during the bone registration process, step S301 is performed, i.e., moving the trackable element towards the registration point of interest. During the performing of step S301, step S302 is also performed: determining, by the control system, whether the torque sensors of each joint operate normally. If not, stopping the automatic operation mode or the auxiliary operation mode, and changing to manual registration S303, i.e., driving the trackable element to perform bone registration by manual operation of the operator. If so, executing step S304: continuing to control the robotic arm to drive the trackable element to move towards the registration point by the control system, and determining whether the cartilage puncture force is equal to or greater than a calibration value, i.e., whether the torque value fed back by the six-axis sensor is equal to or greater than a calibration value. If the cartilage puncture force is equal to or greater than a calibration value, it indicates that the trackable element has punctured the cartilage to reach the bone surface and the registration point on the bone is correctly selected and the bone registration for the next registration point S305 can be performed. If the cartilage puncture force is less than a calibration value, performing S306: continuing to drive the trackable element to puncture cartilage and other tissues. During the process of S306, step S304 is returned to and performed at any time until the cartilage puncture force is equal to or greater than a calibration value.

In this embodiment, two empirical thresholds can be set in the control system. The first threshold is a threshold for mutual verification of sensors, and the second threshold is configured to determine whether the torque sensor exceeds its range. The control system determines whether the sensors on each joint module operate normally according to the two thresholds. Specifically, the control system compares the measured force applied to the robotic arm terminal according to the detection model of the dual encoder with the force applied to the robotic arm terminal measured by the six-axis sensor. If the deviation of the two forces exceeds the range defined by the first threshold, it indicates that sensors are abnormal, and relevant parameters of sensors need to be updated. If the deviation of the two forces is within the range of the first threshold, it indicates that the sensor operates normally, and the data detected by the force identification system can be used subsequently to control the insertion depth of the into the cartilage. The present disclosure does not limit the specific value of the two thresholds that can be determined through experiments according to the requirements of the performance and detection accuracy of the sensor.

In order to further ensure the reliability of the force identification system during actual use after leaving factory, the surgical robot 10 of this embodiment also provides a maintenance function for the force identification system before surgery.

Figure 10:
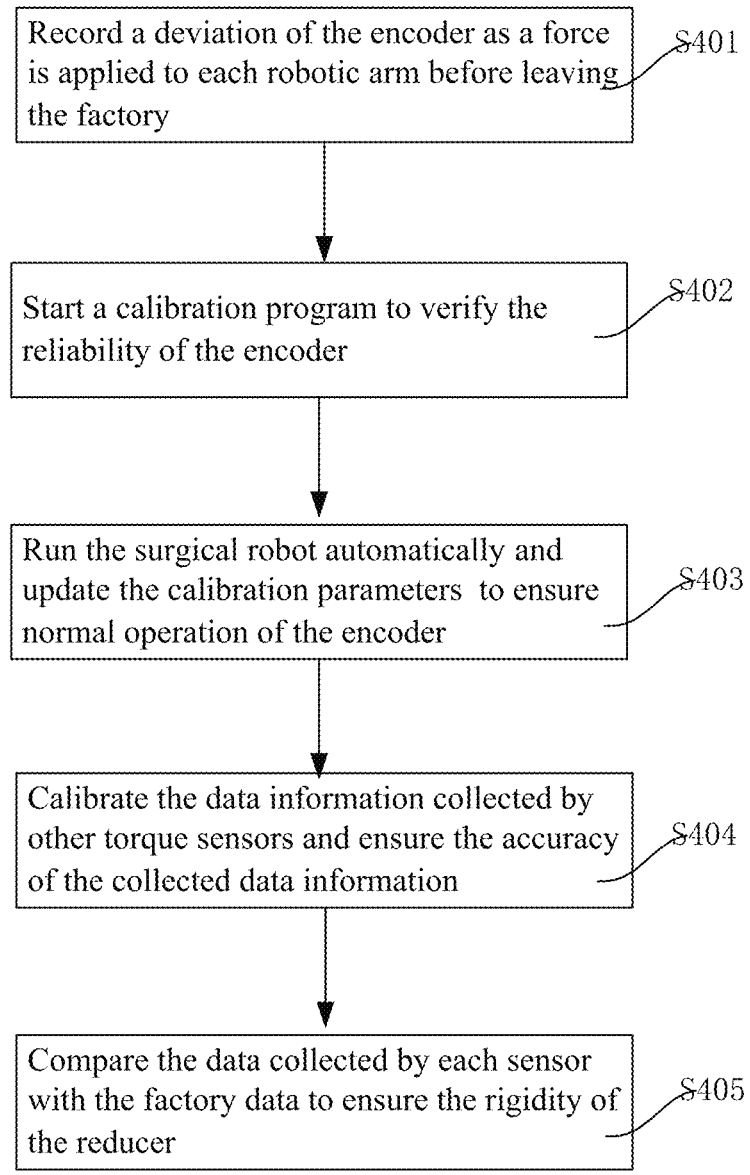
FIG. 10 is a flowchart of an ex-works maintenance calibration of a torque sensor according to an embodiment of the present disclosure.

FIG. 10 is a flowchart for maintenance of a force identification system according to an embodiment of the present disclosure. As shown in FIG. 10, in step S401, before leaving the factory, the deviation of the encoder is recorded as a force is applied to each robotic arm joint and is stored in the control system. In step S402, before leaving the factory, a calibration program is started to verify the reliability of the encoder. After the calibration, in step S403, the surgical robot is automatically run and the calibration parameters are updated to ensure normal operation of the encoder. Correspondingly, before leaving the factory, in step S404, it is also necessary to calibrate the data information collected by other torque sensors and ensure the accuracy of the collected data information, that is, it is also necessary to update the parameters of each sensor on the joint module according to the six-axis sensor, and ensure the accuracy of these parameters. Furthermore, after leaving the factory, step S405 may be performed before surgery during actual use. In step S405, comparing the data collected by each sensor with the factory data to ensure the rigidity of the reducer.

It should be noted that the present disclosure mainly directs to checks of the main mechanical components (i.e., the harmonic reducer) in the surgical robot, to ensure the normal operation state of the harmonic reducer. In stiffness confirmation, since the database records the empirical value ranges of the different stiffness of each robot product, it is able to determine whether the torque sensor operates normally after using a period of time according to the service time of the robot product and the empirical value ranges, and parameters of the original mechanical and hardware design.

Further, a third threshold may be set in the control system. If the detection result of the torque sensor exceeds the third threshold, it is considered that the torque sensor cannot meet the required accuracy, and re-maintenance and re-calibration or the replacement of the torque sensor is needed. The third threshold is determined based on the empirical value ranges of the different stiffness of each robot product, service time of the robot product, and parameters of original mechanical and hardware design such as resolution and accuracy of the dual encoder, resolution, zero drift, or temperature drift of the torque sensor and six-axis torque sensor, stiffness, reduction ratio or reduction ratio error of the harmonic reducer, and stiffness model of the connector.

Through the above confirmation, the torque calculated by the torque sensor model composed of the harmonic reducer and the dual encoder is ensured to be reliable, which is able to be used in the aforementioned protection process and calibration process.

In some embodiments, the control system of the surgical robot 10 uses a neural network calculation method to update the sensor model parameters. Specifically, The six-axis sensor adds online neural network learning and updates the sensor model parameters. This neural network calculation method is able to provide online model parameter update, ensuring a more reliability of the force applied to each rotary joint, and further improving the reliability of the force identification system. A flowchart of the online model parameter update using a six-axis sensor is shown in FIG. 11.

Figure 11:
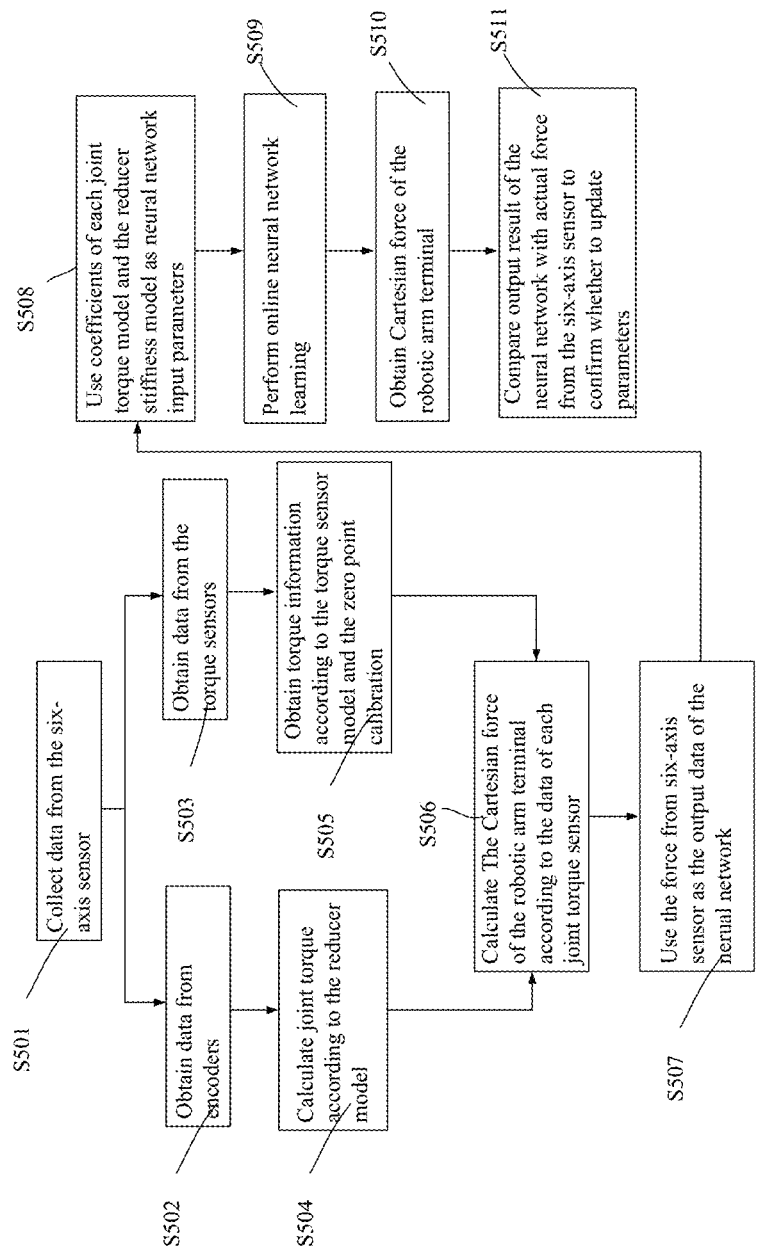
FIG. 11 is a flowchart of an online model parameter update using a six-axis sensor according to an embodiment of the present disclosure.

As shown in FIG. 11, in the neural network learning, the data fed back by the six-axis sensor needs to be collected in advance in step S501. At the same time, the data of the encoder and the data of the torque sensor need to be obtained in step S502 and step S503, respectively. Then, in step S504, the joint torque is obtained according to the encoder data, and in step S505, the torque information is obtained according to the torque sensor model and the zero point calibration. Subsequently, the Cartesian force of the robotic arm terminal is calculated according to the data of each joint torque sensor. The Cartesian force of the robotic arm terminal is the output data of the neural network. More specifically, in step S508, the coefficients of each joint torque model and the reducer stiffness model are used as neural network input parameters; in step S509, online neural network learning is performed using the input parameters; in step S510, the Cartesian force of the robotic arm terminal is obtained; and in step S511, the output result of the neural network is compared with the actual data collected by the six-axis sensor to confirm whether to update the model parameters of the sensor.

Figure 12:
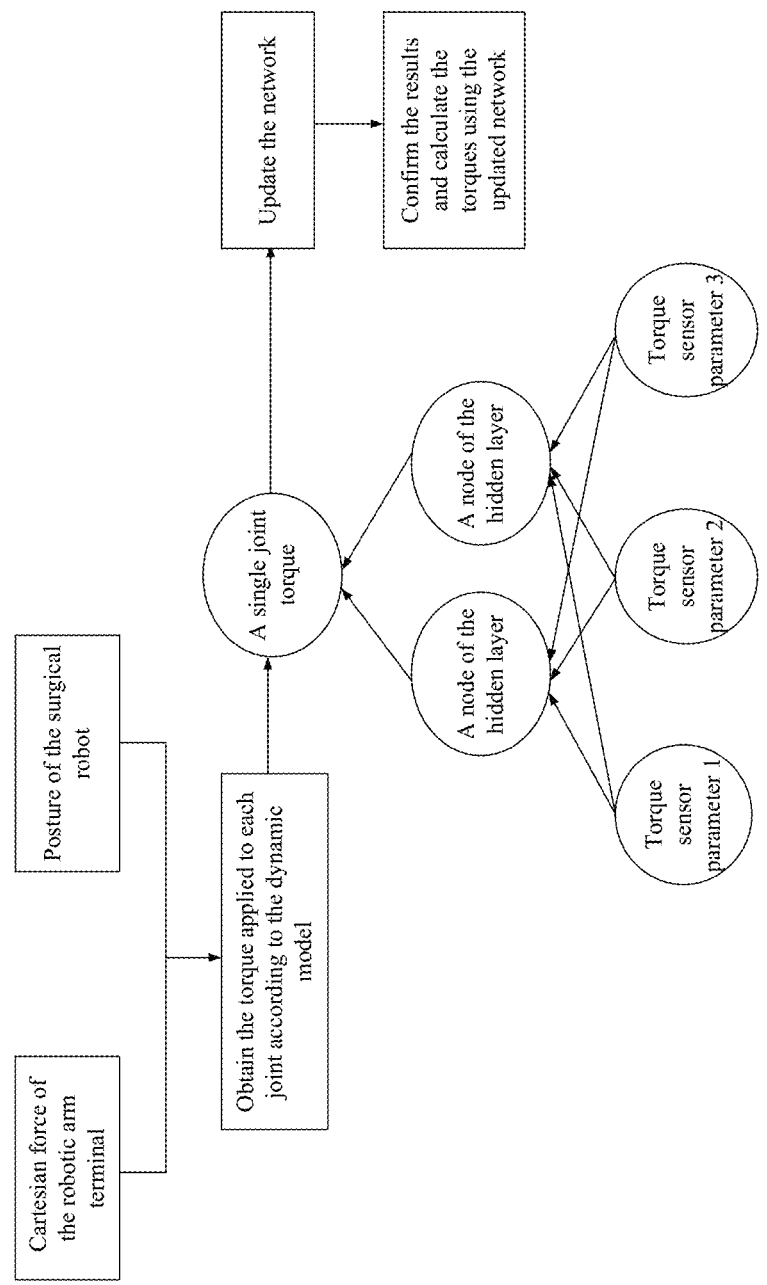
FIG. 12 and FIG. 13 show principles of parameter updates using neural networks according to embodiments of the present disclosure.

FIG. 12 is a process diagram of the obtaining of a torque sensor model based on a neural network model according to a preferred embodiment. As shown in FIG. 12, the neural network has a three-layer structure consisting of an input layer, a hidden layer, and an output layer. The input layer has three nodes, which are torque sensor parameters 1, 2, and 3. The hidden layer has two nodes; and the output layer has one node configured to output a single joint torque. Among them, if a dual encoder is used, the input of the three nodes of the input layer respectively corresponds to the stiffness of the harmonic reducer, the angular velocity of the joint and the angular position of the joint; if a torque sensor is used, the input parameters are the torque conversion coefficient, zero point of torque sensor and temperature of torque sensor. The node of the output layer outputs the actual torque of the torque sensor.

In this embodiment, a neural network model after online training is adopted, that is, the weights and thresholds of all nodes are obtained through sample training before leaving the factory. During using a surgical robot, the model parameters in the neural network are continuously updated. The specific training method may be a gradient descent method or other existing technologies, which is not limited in the present disclosure.

Figure 13:
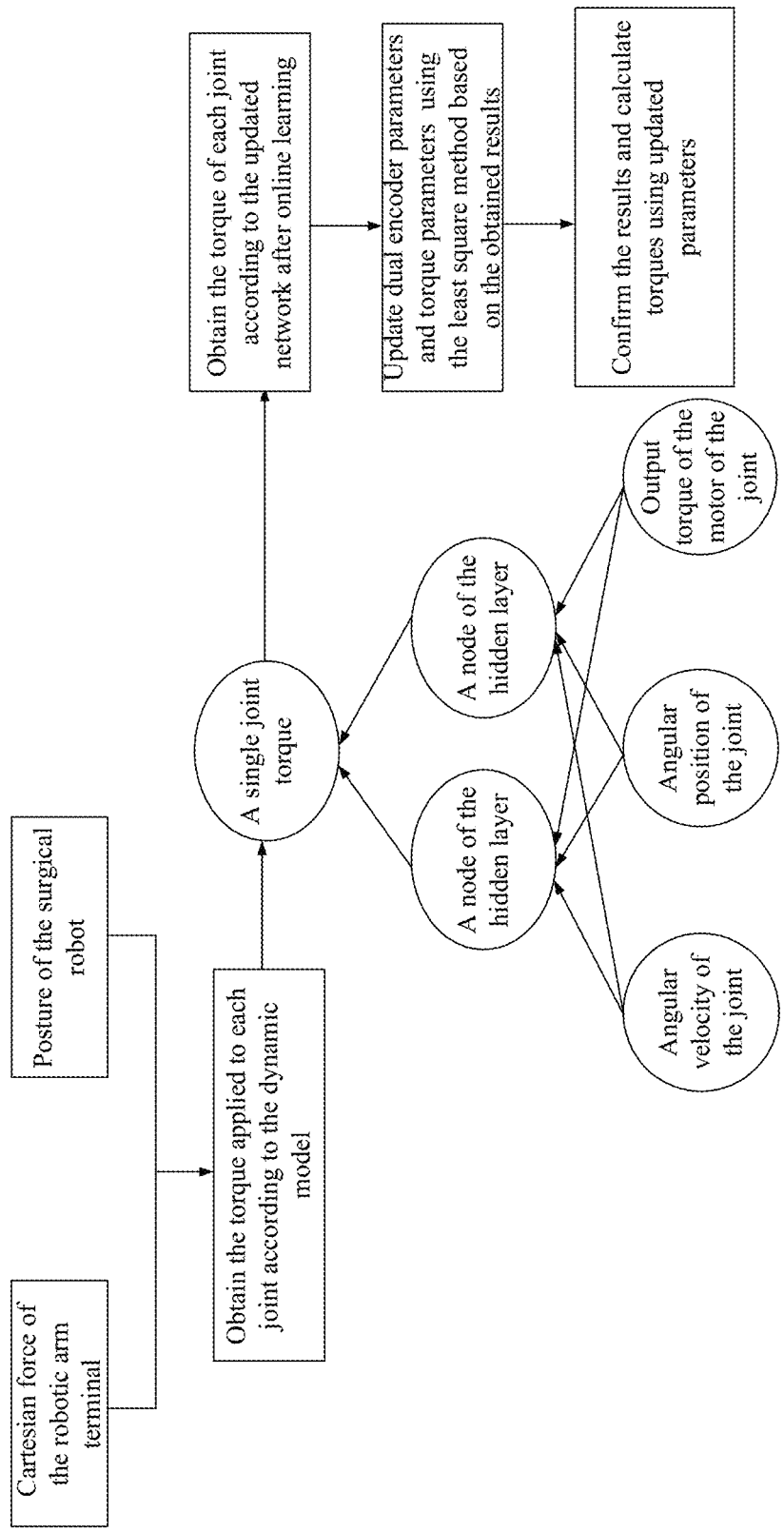

In addition to the neural network model mentioned in FIG. 12, the present disclosure also provides a model update method that is more close to the actual physical meaning, which can refer to FIG. 13.

As shown in FIG. 13, the neural network has a three-layer structure consisting of an input layer, a hidden layer, and an output layer. The input layer has three nodes, the hidden layer has two nodes, and the output layer has one node. The inputs of three nodes of the input layer respectively correspond to the angular velocity of the joint, the angular position of the joint, and the output torque of the motor of the joint. The node of the output layer outputs the actual torque of the torque sensor. After updating the model, according to the obtained torque results, the parameter coefficients of the dual encoder torque model and the parameter coefficients of the torque sensor are updated using the least square method, and the updated coefficients are used to calculation confirmation.

Further, the control system of this embodiment includes a memory and a processor, the memory having a program stored therein to make the processor achieve the above functions by running the program.

In summary, in embodiments of the present disclosure, the surgical robot utilizes a force identification system to achieve the purpose of the surgical robot to automatically complete or assist in completing bone registration, which greatly improves the efficiency of bone registration and improves accuracy and success rate of bone registration. Further, various force identification devices are used to ensure the accuracy of cartilage penetration force during the operation, thereby improving the accuracy of the operation. Furthermore, the surgical robot also provides a maintenance method after leaving the factory, which is able to effectively protect the core components of the surgical robot and confirm the operation status and component status of the robot to ensure that no problem occurs during the operation. Furthermore, for the six-axis sensor, the surgical robot also provides a method of online neural network learning to update model parameters. This method is able to provide update of the online model parameter to ensure a more reliable force situation of each joint, further improving the reliability of the force identification system.

In particular, the surgical robot also has an online verification function that is able to verify the machine after leaving the factory, ensuring a preoperative perfect condition of the robot and a successful execution of the surgical process.

The above description only described the preferred embodiments of the present disclosure, and is not intended to limit the scope of the present disclosure. Any changes and modifications made by those skilled in the art according to the above disclosure are all within the protection scope of the appended claims.

What is claimed is:

1. A method for bone registration of a surgical robot, comprising:

selecting a registration point of interest on an object according to a navigation system, and providing information of the selected registration point of interest on the object to a robotic arm system;

controlling movements of a robotic arm in the robotic arm system to drive a trackable element to move to the registration point of interest on the object by the robotic arm;

acquiring a force applied to a robotic arm terminal, the force detected by a force identification system; and determining whether the trackable element has moved to the registration point of interest on the object according to the force applied to the robotic arm terminal;

wherein the step of determining whether the trackable element has moved to the registration point of interest on the object according to the force applied to the robotic arm terminal comprises:

determining whether the force identification system operates normally according to the force detected by the force identification system, and if so, controlling the robotic arm to drive the trackable element to move towards the registration point of interest.

2. The method for bone registration of a surgical robot according to claim 1, further comprising:

acquiring a current position of the trackable element tracked by the navigation system; and determining whether the trackable element has moved to the registration point of interest on the object according to the current position of the trackable element.

3. The method for bone registration of a surgical robot according to claim 2, wherein the step of determining whether the trackable element has moved to the registration point of interest on the object according to the force applied to the robotic arm terminal has a high priority, and the step of determining whether the trackable element has moved to the registration point of interest on the object according to the current position of the trackable element has a low priority.

4. The method for bone registration of a surgical robot according to claim 1, after the step of controlling the robotic arm to drive the trackable element to move towards the registration point upon the determination of the force identification system operating normally, the method further comprising:

comparing the force applied to the robotic arm terminal with a calibration value; and determining that the trackable element has moved to the registration point of interest on the object if the force applied to the robotic arm terminal is equal to or greater than the calibration value, or otherwise keeping controlling the robotic arm to drive the trackable element to move towards the registration point of interest until the force applied to the robotic arm terminal is equal to or greater than the calibration value.

5. The method for bone registration of a surgical robot according to claim 1, comprising the following steps after determining that the trackable element has moved to the registration point of interest on the object:

determining whether the navigation system is able to track position of the trackable element normally; and if so, controlling the robotic arm to drive the trackable element to move to a next registration point of interest, or otherwise, controlling the robotic arm to adjust a pose of the trackable element until the navigation system is able to track position of the trackable element normally.

6. The method for bone registration of a surgical robot according to claim 1, comprising the following step before controlling the robotic arm to move:
   planning a movement trajectory by the robotic arm system based on the registration point of interest on the object selected by the navigation system, and driving the trackable element to move to the registration point of interest along the movement trajectory by the robotic arm.

7. The method for bone registration of a surgical robot according to claim 1, comprising the following step before the step of determining whether the trackable element has moved to the registration point of interest on the object:
   calculating a force applied to the robotic arm terminal according to forces applied to each robotic arm joints acquired by the force identification system;
   acquiring a force applied to the robotic arm terminal by the force identification system;
   comparing the calculated force applied to the robotic arm terminal with the acquired force applied to the robotic arm terminal; and
   updating the force identification system when a deviation between the calculated force applied to the robotic arm terminal and the acquired force applied to the robotic arm terminal is beyond a predetermined range.

8. The method for bone registration of a surgical robot according to claim 7, wherein the forces applied to the respective robotic arm joints are acquired by:
   detecting a force applied to each of the robotic arm joints by using a first sensor mounted thereon; and
   wherein the step of acquiring a force applied to the robotic arm terminal by the force identification system comprises:
   detecting a force applied to the robotic arm terminal by using a second sensor mounted at the robotic arm terminal.

9. The method for bone registration of a surgical robot according to claim 7, wherein the force applied to the robotic arm terminal is calculated by a neural network calculation method, and
   the method comprising: before output of the calculated force applied to the robotic arm terminal, performing a neural network training on the force identification system and maintaining a network structure and a weight file after the neural network training.

10. A surgical robot, comprising a control system, a force identification system, a robotic arm system and a navigation system, the robotic arm system comprising a robotic arm with a robotic arm terminal configured to connect to a trackable element, the control system communicatively connected with the force identification system, the robotic arm system and the navigation system, the navigation system communicatively connected with the robotic arm system;
   wherein the navigation system is configured to provide information of a registration point of interest on an object to the robotic arm system, and the robotic arm system is configured to control movements of the robotic arm to drive the trackable element to move to the registration point of interest on the object based on the information of the registration point of interest on the object; and
   wherein the force identification system is mounted on the robotic arm and is configured to detect a force applied to the robotic arm terminal and provide the detected force applied to the robotic arm terminal to the control system, and the control system is configured to determine whether the trackable element has moved to the registration point of interest on the object according to the force applied to the robotic arm terminal;
   wherein the step of determining whether the trackable element has moved to the registration point of interest on the object according to the force detected to the robotic arm terminal comprises:
   determining whether the force identification system operates normally according to the force detected by the force identification system, and if so, controlling the robotic arm to drive the trackable element to move towards the registration point of interest.

11. The surgical robot according to claim 10, wherein the navigation system is configured to acquire a current position information of the trackable element and provide the current position information to the control system; and wherein the control system is configured to determine whether the trackable element has moved to the registration point of interest on the object according to the current position information of the trackable element.

12. The surgical robot according to claim 11, wherein the control system is configured such that determination of whether the trackable element has moved to the registration point of interest on the object according to the force applied to the robotic arm terminal has a high priority and determination of whether the trackable element has moved to the registration point of interest on the object according to the current position information of the trackable element has a low priority.

13. The surgical robot according to claim 10, wherein upon the determination of the force identification system operating normally, the control system is configured to compare the force applied to the robotic arm terminal with a calibration value pre-stored in the control system;
   if the force applied to the robotic arm terminal is equal to or greater than the calibration value, the control system determines that the trackable element have moved to the registration point of interest on the object;
   if the force applied to the robotic arm terminal is less than the calibration value, the control system keeps to control the robotic arm to drive the trackable element to move towards the registration point until the force applied to the robotic arm terminal is equal to or greater than the calibration value.

14. The surgical robot according to claim 10, wherein after determination of the trackable element having moved to the registration point of interest on the object, the control system is further configured to determine whether the navigation system is able to track position of the trackable element normally;
   if so, the control system controls the robotic arm to drive the trackable element to move to a next registration point of interest;
   or otherwise, the control system controls the robotic arm to adjust a pose of the trackable element until the navigation system is able to track the position of the trackable element normally.

15. The surgical robot according to claim 10, wherein the robotic arm comprises a plurality of robotic arm joints, and the force identification system comprises a first force identification device and a second force identification device;
   wherein the first force identification device comprises a plurality of first sensors, and each of the robotic arm joints is provided with at least one of the first sensors; and wherein each first sensor is configured to detect a force applied to a corresponding robotic arm joint of the robotic arm joints;

wherein the second force identification device comprises at least one second sensor mounted at the robotic arm terminal, the second sensor configured to detect a force applied to the robotic arm terminal; and wherein the control system is configured to:

calculate a force applied to the robotic arm terminal according to forces applied to respective robotic arm joints detected by the plurality of first sensors;

compare the calculated force applied to the robotic arm terminal with the detected force applied to the robotic arm terminal; and update the force identification system when a deviation between the calculated force applied to the robotic arm terminal and the detected force applied to the robotic arm terminal is beyond a predetermined range.

16. The surgical robot according to claim 15, wherein each of the plurality of robotic arm joints has a dual encoder mounted thereon, the dual encoder comprising an absolute encoder and an incremental encoder; wherein the robotic arm further comprises, a driver and a reducer for driving at least one of the robotic arm joints, an output of the driver coupled to an input of the reducer, an output of the reducer coupled to the robotic arm joint; and wherein one of the absolute encoder and the incremental encoder is provided at the input of the reducer and the other one of the absolute encoder and the incremental encoder is provided at the output of the reducer.

17. The surgical robot according to claim 16, wherein a force $\tau$ applied to the robotic arm joint is calculated according to:

$$\tau = K\delta$$
$$\delta = \frac{T1}{c1} - \left(\frac{T2}{c2} + S0\right).$$

where K is a stiffness coefficient of the reducer; $\delta$ is a deformation amount of the robotic arm joint; T1 is an absolute position of the robotic arm joint fed back by the absolute encoder; T2 is a relative position of the robotic arm joint fed back by the incremental encoder; c1 is a resolution of the absolute encoder; c2 is a resolution of the incremental encoder; S0 is a startup initialization position of the incremental encoder.

18. The surgical robot according to claim 17, wherein the dual encoder is communicatively connected with the control system; and wherein the control system is configured to obtain a force applied to the robotic arm joint according to a relationship between a data deviation of the dual encoder and the force applied to the robotic arm joint.

* * * * *